(12) United States Patent
Heyninck-Jantz et al.

(10) Patent No.: US 7,682,304 B2
(45) Date of Patent: Mar. 23, 2010

(54) COMPOSITE HEART VALVE APPARATUS MANUFACTURED USING TECHNIQUES INVOLVING LASER MACHINING OF TISSUE

(75) Inventors: Christine Heyninck-Jantz, Tustin, CA (US); Debra Taitague, Orange, CA (US); Tomas R. McNatt, Irvine, CA (US)

(73) Assignee: Medtronic, Inc., Minneapolis, MN (US)

( * ) Notice: Subject to any disclaimer, the term of this patent is extended or adjusted under 35 U.S.C. 154(b) by 613 days.

(21) Appl. No.: 11/523,163

(22) Filed: Sep. 19, 2006

(65) Prior Publication Data

US 2007/0073392 A1    Mar. 29, 2007

Related U.S. Application Data

(60) Provisional application No. 60/719,151, filed on Sep. 21, 2005.

(51) Int. Cl.
*A61F 2/04*    (2006.01)
(52) U.S. Cl. .......................... 600/36; 623/2.1
(58) Field of Classification Search ............. 600/36; 623/1.13, 1.24–2.1, 3–2.19, 2.38, 901, 910, 623/902; 264/400; 128/898
See application file for complete search history.

(56) References Cited

U.S. PATENT DOCUMENTS

| | | | |
|---|---|---|---|
| 4,655,771 A | 4/1987 | Wallsten | |
| 4,791,927 A | 12/1988 | Menger | |
| 4,793,344 A | 12/1988 | Cumming et al. | |
| 4,862,886 A | 9/1989 | Clarke et al. | |
| 5,125,922 A | 6/1992 | Dwyer et al. | |
| 5,144,630 A | 9/1992 | Lin | |
| 5,163,955 A | 11/1992 | Love et al. | |
| 5,180,378 A | 1/1993 | Kung et al. | |
| 5,188,632 A * | 2/1993 | Goldenberg | 606/7 |
| 5,232,366 A | 8/1993 | Levy | |
| 5,288,288 A | 2/1994 | Lewis et al. | |
| 5,368,608 A | 11/1994 | Levy et al. | |
| 5,415,667 A | 5/1995 | Frater | |
| 5,451,221 A | 9/1995 | Cho et al. | |

(Continued)

FOREIGN PATENT DOCUMENTS

EP    1057460    12/2000

(Continued)

OTHER PUBLICATIONS

"ablate." Mosby's Dictionary of Medicine, Nursing, & Health Professions. Philadelphia: Elsevier Health Sciences, 2006. Credo Reference. Feb. 9, 2009 <http://www.credoreference.com/entry/6655723/.>.*

(Continued)

*Primary Examiner*—Charles A Marmor, II
*Assistant Examiner*—Carrie Harris
(74) *Attorney, Agent, or Firm*—Mike Jaro; Jeffrey J. Hohenshell

(57) ABSTRACT

Methodology for using laser machining techniques to modify a tissue for use in a medical device. In a representative mode of practice, relatively low energy laser machining is used to thin down at least a portion of a valved jugular vein. The thinned down vein may then be sutured to, or otherwise integrated with, a corresponding stent to make a percutaneous heart valve.

9 Claims, 6 Drawing Sheets

U.S. PATENT DOCUMENTS

| | | | |
|---|---|---|---|
| 5,468,238 | A | 11/1995 | Mersch |
| 5,480,424 | A | 1/1996 | Cox |
| 5,481,619 | A | 1/1996 | Schwartz et al. |
| 5,489,298 | A | 2/1996 | Love et al. |
| 5,505,727 | A | 4/1996 | Keller |
| 5,549,600 | A | 8/1996 | Cho |
| 5,554,184 | A | 9/1996 | Machiraju |
| 5,562,842 | A | 10/1996 | Laferriere |
| 5,564,440 | A | 10/1996 | Swartz et al. |
| 5,588,967 | A | 12/1996 | Lemp et al. |
| 5,611,797 | A | 3/1997 | George |
| 5,646,733 | A | 7/1997 | Bieman |
| 5,716,399 | A | 2/1998 | Love |
| 5,722,972 | A | 3/1998 | Power et al. |
| 5,730,156 | A | 3/1998 | Mackool |
| 5,742,626 | A | 4/1998 | Mead et al. |
| 5,757,950 | A | 5/1998 | Bruder |
| 5,769,840 | A | 6/1998 | Schirmer |
| 5,807,385 | A | 9/1998 | Keller |
| 5,840,075 | A | 11/1998 | Mueller et al. |
| 5,849,006 | A | 12/1998 | Frey et al. |
| 5,855,597 | A | 1/1999 | Jayaraman |
| 5,855,620 | A | 1/1999 | Bishopric et al. |
| 5,871,462 | A | 2/1999 | Yoder et al. |
| 5,875,004 | A | 2/1999 | Yamane et al. |
| 5,908,416 | A | 6/1999 | Costello et al. |
| 5,921,980 | A | 7/1999 | Kirn |
| 5,922,027 | A | 7/1999 | Stone |
| 5,938,954 | A | 8/1999 | Onuma et al. |
| 5,957,915 | A | 9/1999 | Trost |
| 5,982,945 | A | 11/1999 | Neff et al. |
| 5,989,243 | A | 11/1999 | Goldenberg |
| 6,057,525 | A | 5/2000 | Chang et al. |
| 6,129,758 | A | 10/2000 | Love |
| 6,136,023 | A | 10/2000 | Boyle |
| 6,161,543 | A | 12/2000 | Cox et al. |
| 6,165,170 | A * | 12/2000 | Wynne et al. .................. 606/9 |
| 6,193,749 | B1 | 2/2001 | Schroeder et al. |
| 6,251,328 | B1 * | 6/2001 | Beyer et al. ................. 264/400 |
| 6,378,221 | B1 | 4/2002 | Ekholm, Jr. et al. |
| 6,528,006 | B1 | 3/2003 | Jansen |
| 6,553,681 | B2 | 4/2003 | Ekholm, Jr. et al. |
| 6,558,372 | B1 | 5/2003 | Altshuler |
| 6,613,087 | B1 | 9/2003 | Healy et al. |
| 6,641,609 | B2 | 11/2003 | Globerman |
| 6,652,578 | B2 | 11/2003 | Bailey et al. |
| 6,656,219 | B1 | 12/2003 | Wiktor |
| 6,682,559 | B2 | 1/2004 | Myers et al. |
| 6,719,789 | B2 | 4/2004 | Cox |
| 6,755,819 | B1 | 6/2004 | Waelti |
| 6,773,455 | B2 | 8/2004 | Allen et al. |
| 6,805,711 | B2 | 10/2004 | Quijano et al. |
| 6,830,585 | B1 | 12/2004 | Artof et al. |
| 6,872,226 | B2 | 3/2005 | Cali et al. |
| 6,911,043 | B2 | 6/2005 | Myers et al. |
| 6,932,808 | B2 | 8/2005 | Gross |
| 6,939,359 | B2 | 9/2005 | Tu et al. |
| 6,939,378 | B2 * | 9/2005 | Fishman et al. .............. 623/4.1 |
| 6,971,394 | B2 | 12/2005 | Sliwa, Jr. et al. |
| 7,037,333 | B2 | 5/2006 | Myers et al. |
| 7,060,103 | B2 | 6/2006 | Carr, Jr. et al. |
| 2002/0091441 | A1 | 7/2002 | Guzik |
| 2002/0103542 | A1 | 8/2002 | Bilbo |
| 2003/0023303 | A1 | 1/2003 | Palmaz et al. |
| 2003/0036791 | A1 | 2/2003 | Philipp et al. |
| 2003/0199963 | A1 | 10/2003 | Tower et al. |
| 2003/0199971 | A1 | 10/2003 | Tower et al. |
| 2004/0000540 | A1 | 1/2004 | Soboyejo et al. |
| 2004/0048796 | A1 | 3/2004 | Hariri et al. |
| 2006/0206202 | A1 | 9/2006 | Bonhoeffer et al. |
| 2007/0254005 | A1 * | 11/2007 | Pathak et al. ................ 424/423 |

FOREIGN PATENT DOCUMENTS

| | | |
|---|---|---|
| WO | 99/30884 | 6/1999 |
| WO | WO01/26587 | 4/2001 |

OTHER PUBLICATIONS

Bonhoeffer et al., "Percutaneous Insertion of the Pulmonary Valve," *Journal of the American College of Cardiology*, vol. 39, No. 10, pp. 1664-1669, 2002.

Bonhoeffer et al., "Transcatheter Replacement of a Bovine Valve in Pulmonary Position: A Lamb Study," *Circulation*, 102, pp. 813-816, Aug. 15, 2000.

Boudjemline et al., "Future Trends: Percutaneous Valve Implantation: Past, Present and Future," *Heart Views*, vol. 3, No. 2, Jun.-Aug. 2002.

Boudjemline et al., Percutaneous aortic valve replacement: will we get there? *Heart* 2001; 86:705-706, Dec.

Doi et al., "Novel compliant and tissue-permeable microporous polyurethane vascular prosthesis fabricated using an excimer laser ablation technique," *Journal of Biomedical Material Research*, vol. 31, Issue 1, pp. 27-33, 1995 (abstract only).

Gilad et al., "Percutaneous Heart Valves: The Emergence of a Disruptive Technology," *Technology Review*, vol. 82, No. 3, pp. 199-201, May 2005.

Borsuztky et al., "Tunable UV Radiation at Short Wavelengths (188-240 nm) Generated by Frequency Mixing in Lithium Borate," *Appl. Phys.*, B62, 380-384, 1991.

http://www.ctsnet.org/sections/innovation/valvetechnology/articles/article-6.html, printed Sep. 14, 2005, Revuelta, J.M., "Percutaneous Heart Valve Therapy: A New Step Toward Off-Pump Cardiac Surgery or Interventional Cardiology?" (3 pages).

"Quality Cutting of Pericardial Tissue for Edwards Lifesciences," http://gram.eng.uci.edu/~ghubbard/mae188/index_files/EdwardsLifesciences.PDF, Jun. 14, 2000.

* cited by examiner

COMPOSITE HEART VALVE APPARATUS MANUFACTURED USING TECHNIQUES INVOLVING LASER MACHINING OF TISSUE

PRIORITY CLAIM

The present non-provisional patent Application claims priority under 35 USC §119(e) from U.S. Provisional Patent Application having Ser. No. 60/719151, filed on Sep. 21, 2005, by Heyninck-Jantz, and titled COMPOSITE HEART VALVE APPARATUS MANUFACTURED USING TECHNIQUES INVOLVING LASER MACHINING OF TISSUE, wherein the entirety of said provisional patent application is incorporated herein by reference for all purposes.

FIELD OF THE INVENTION

The present invention relates to a composite medical device, e.g., a heart valve apparatus, incorporating components derived from tissue and nontissue sources, wherein laser ablation techniques are used to prepare a tissue for incorporation into the apparatus. Preferred embodiments in the form of a composite heart valve apparatus are useful in the treatment of diseased or injured heart valves.

BACKGROUND OF THE INVENTION

Tissue is used as a component source in several kinds of medical devices. In some of these applications, it may be desirable to modify the thickness and/or surface characteristics of tissue by removing all or a portion of one or more layers of the tissue. Often, unwanted tissue is removed and discarded while the remainder is incorporated into the device. Percutaneous heart valves are an exemplary application that involves thinning down of tissue before the tissue is incorporated into a heart valve.

As background, there are four valves in the heart that serve to direct blood flow through the two sides of the heart. On the left (systemic) side of the heart are: (1) the mitral valve, located between the left atrium and the left ventricle, and (2) the aortic valve, located between the left ventricle and the aorta. These two valves direct oxygenated blood from the lungs through the left side of the heart and into the aorta for distribution to the body. On the right (pulmonary) side of the heart are: (1) the tricuspid valve, located between the right atrium and the right ventricle, and (2) the pulmonary valve, located between the right ventricle and the pulmonary artery. These two valves direct de-oxygenated blood from the body through the right side of the heart and into the pulmonary artery for distribution to the lungs, where the blood becomes re-oxygenated in order to begin the circuit anew.

All four of these heart valves are passive structures in that they do not themselves expend any energy and do not perform any active contractile function. They consist of moveable "leaflets" that open and close in response to differential pressures on either side of the valve. The mitral and tricuspid valves are referred to as "atrioventricular valves" because they are situated between an atrium and ventricle on each side of the heart. The mitral valve has two leaflets and the tricuspid valve has three. The aortic and pulmonary valves are referred to as "semilunar valves" because of the unique appearance of their leaflets, which are shaped somewhat like a half-moon and are more aptly termed "cusps". The aortic and pulmonary valves each have three cusps.

Heart valves may exhibit abnormal anatomy and function as a result of congenital or acquired valve disease. Congenital valve abnormalities may be well-tolerated for many years only to develop into a life-threatening problem in an elderly patient, or may be so severe that emergency surgery is required within the first few hours of life. Acquired valve disease may result from causes such as rheumatic fever, degenerative disorders of the valve tissue, bacterial or fungal infections, and trauma.

Since heart valves are passive structures that simply open and close in response to differential pressures on either side of the particular valve, the problems that can develop with valves can be classified into two categories: (1) stenosis, in which a valve does not open properly, and (2) insufficiency (also called regurgitation), in which a valve does not close properly. Stenosis and insufficiency may occur concomitantly in the same valve or in different valves. Both of these abnormalities increase the workload placed on the heart. The severity of this increased stress on the heart and the patient, and the heart's ability to adapt to it, determine whether the abnormal valve will have to be surgically replaced (or, in some cases, repaired).

Valve repair and valve replacement surgery is described and illustrated in numerous books and articles, and a number of options, including artificial mechanical valves and artificial tissue valves, are currently available. Prosthetic heart valves are described, for example, in U.S. Patent Publication No. 2004/0138742 A1.

Recently, there has been interest in minimally invasive and percutaneous replacement of cardiac valves. Percutaneous replacement of a heart valve does not involve actual physical removal of the diseased or injured heart valve. Rather, the defective or injured heart valve typically remains in position. The replacement valve typically is inserted into a balloon catheter and delivered percutaneously via the vascular system to the location of the failed heart valve.

In the context of percutaneous, pulmonary valve replacement, US Patent Application Publication Nos. 2003/0199971 A1 and 2003/0199963 A1, both filed by Tower, et al. describe a valved segment of bovine jugular vein, mounted within an expandable stent, for use as a replacement pulmonary valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits. Other implantables and implant delivery devices also are disclosed in published U.S. Pat. Application No. 2003-0036791-A1 and European Patent Application No. 1 057 460-A1.

Assignee's co-pending U.S. Provisional Patent Application titled APPARATUS FOR TREATMENT OF CARDIAC VALVES AND METHOD OF ITS MANUFACTURE, in the names of Philippe Bonhoeffer and Debra Ann Taitague et al., filed Nov. 19, 2004, bearing, and assigned U.S. Ser. No. 60/629,468 (hereinafter referred to as the "Bonhoeffer and Taitague Application") describes innovative, percutaneous heart valves for use as a replacement pulmonary valve. Like the valves described by Tower et al., the heart valves of this co-pending application incorporate a valved segment of bovine jugular vein, mounted within an expandable stent.

The tissue source for the percutaneous heart valves described in the Tower, Bonhoeffer, and Bonhoeffer and Taitague Application documents cited herein preferably is a valved segment of a bovine jugular vein. The bovine jugular vein has many properties making it suitable for use in a percutaneous heart valve. However, the size of the venous wall of this bovine tissue tends to be too thick to be used for percutaneous insertion. Fortunately, the wall thickness can be reduced significantly without interfering with the valve function. After removal of unnecessary tissue from the external venous wall, the modified tissue is sutured to a stent. The device is cross-linked with a buffered gluteraldehyde solution, sterilized and stored in an alcoholic gluteraldehyde solution according to industry protocols.

Conventionally, manual techniques are used to reduce the thickness profile of the venous wall. That is, an operator uses appropriate implements to remove unwanted tissue by hand. This process of thinning the venous wall is described in the Tower, Bonhoeffer, and Bonhoeffer and Taitague Application documents cited above. The manual process will produce an excellent product, but it nonetheless suffers from at least two drawbacks. First, the manual modification of the tissue is painstaking and laborious. It would be highly desirable to provide a tissue reduction methodology that can be carried out in less time. Second, the scrap rate of the manual technique can be quite high. It would be highly desirable to provide a tissue reduction methodology that modifies the thickness of the bovine venous wall with much higher yields.

SUMMARY OF THE INVENTION

The present invention provides a methodology for using laser machining techniques to modify a tissue for use in a medical device. In a representative mode of practice, relatively low energy laser machining is used to thin down at least a portion of a valved jugular vein. The thinned down vein may then be sutured to, or otherwise integrated with, a corresponding stent to make a percutaneous heart valve.

In preferred modes of practice, the present invention is particularly directed to improvements in valves generally as described in the Tower et al and Bonhoeffer, et al. references cited above. However, the invention may also be useful in other types of valves, particularly valves which take the form of a generally tubular valve body of natural or synthetic material, in which valve leaflets are provided. Examples of such other valves include those described in U.S. Pat. Nos. 6,719,789 and 5,480,424, both issued to Cox. The methods of the present invention may also be practiced for use with pericardial tissue to remove unwanted layers prior to processing.

The methodology of the invention modifies tissue much faster than wholly manual techniques. Scrap rates are much lower, providing correspondingly higher yields.

In one aspect, the present invention relates to a method of making a composite medical device. Laser energy is used to ablate at least a portion of a tissue. The physical dimensions of the tissue portion are modified to correspond to a nontissue component. Components comprising the ablated tissue and the nontissue component are integrated together to from the composite medical device.

In another aspect, the present invention relates to a method of making a percutaneous heart valve. A tissue comprising a valve is provided. Laser energy is used to thin down at least a portion of a wall of the tissue. The thinned tissue is attached to a stent.

The present invention also relates to percutaneous heart valves made according to the methods of the present invention. The present invention further relates to methods of treating a mammalian patient, comprising the steps of providing a percutaneous heart valve made according to the methods of the present invention and percutaneously implanting the heart valve in the patient.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered references designate like parts throughout the figures thereof, and wherein.

DETAILED DESCRIPTION

Figure 1A:
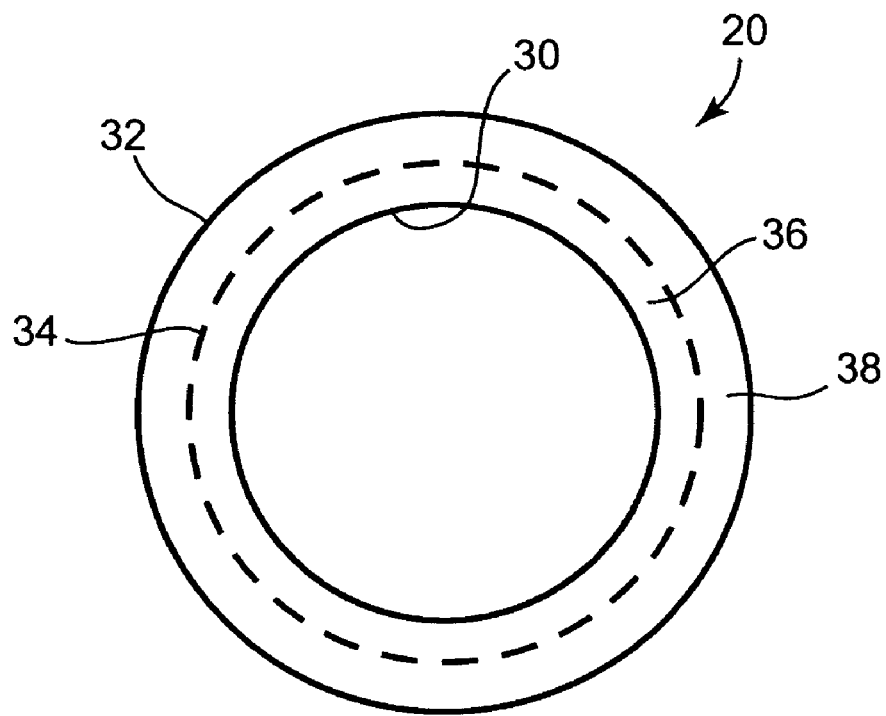
FIG. 1a schematically shows an end view of an unmodified, valved jugular vein, wherein a boundary is provided between wanted and unwanted tissue.
Figure 1B:
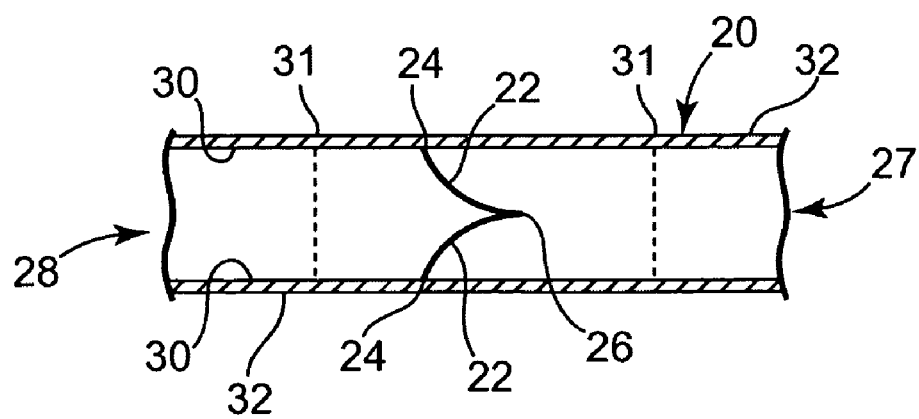
FIG. 1b schematically shows a cross-sectional side view of the vein of FIG. 1.
Figure 1C:
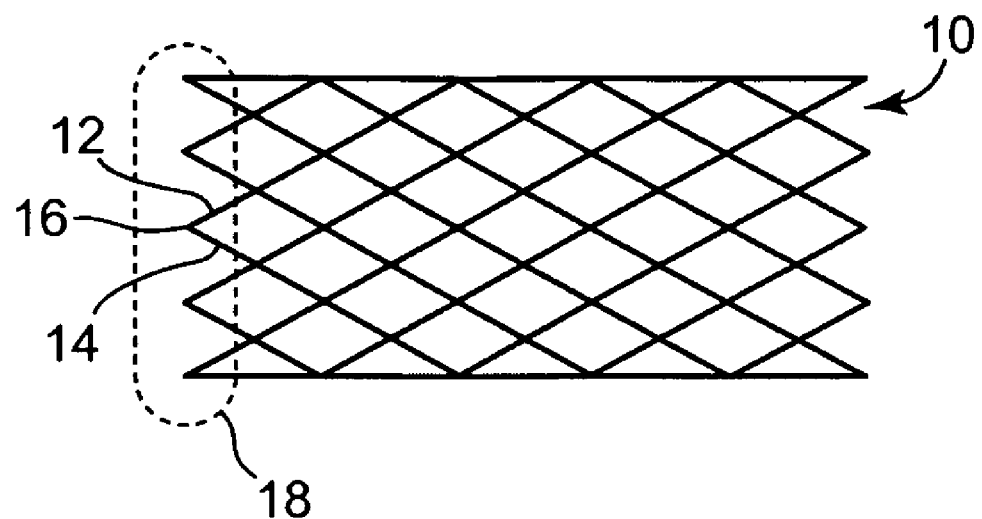
FIG. 1c schematically shows an embodiment of a stent.
Figure 1D:
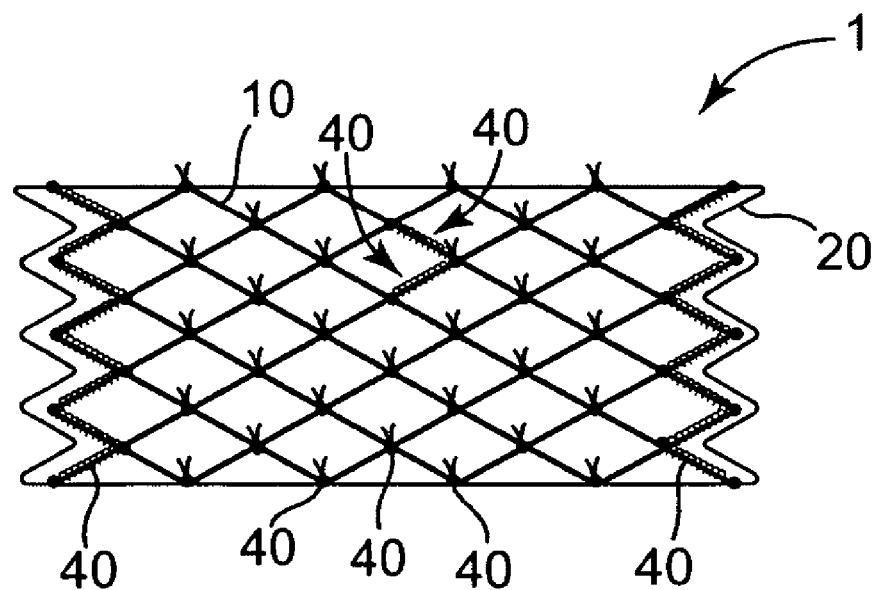
FIG. 1d schematically shows the vein of FIG. 1a incorporated into and sutured to the stent of FIG. 1c to provide a percutaneous heart valve, wherein the vein has been modified in accordance with principles of the present invention using laser ablation techniques.
Figure 2:
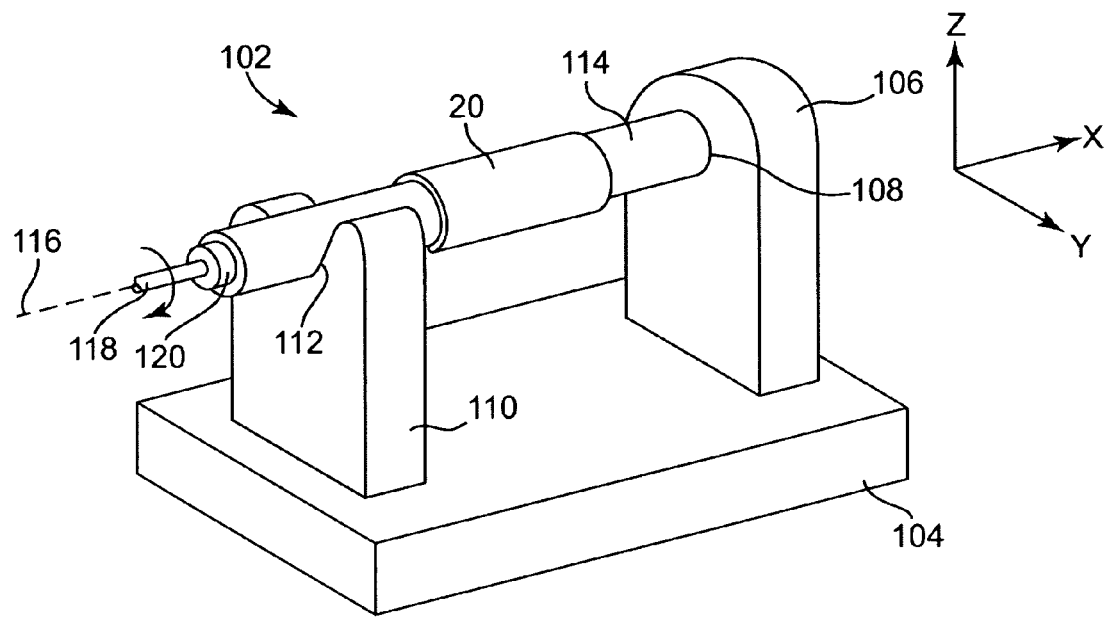
FIG. 2 shows a perspective view of a stage assembly incorporated into a laser machining system of the present invention, wherein the vein of FIG. 1a is supported on the mandrel of the system in order to reduce the thickness profile of the vein using laser ablation techniques.

For purposes of illustration, the present invention will be described in the context of the manufacture of a composite, percutaneous heart valve 1 as shown in FIG. 1d using the components shown schematically in FIGS. 1a, 1b, 1c, and 1d. Heart valve 1 is useful for percutaneous implantation, especially in the pulmonary position for mammalian patients including humans, horses, dogs, and cats. Heart valve 1 is composite in the sense that valve 1 incorporates components derived from both tissue and nontissue sources. FIGS. 1a, 1b, 1c, and 1d show the tissue component in the form of a vein segment 20 incorporating a leaflet-based valve and the nontissue component in the form of stent 10. The vein segment 20 as illustrated includes leaflets 22, extending from the wall of the vein segment 20 from the leaflet bases 24 to commissures 26, which define the outer meeting points of the furthest downstream portions of the leaflets. In use, blood enters the inflow end 28 and exits the outflow end 27 of the vein segment.

The vein segment 20 preferably has three leaflets 22, but may optionally have less or more than this. The leaflets 22 of the vein segment 20, in the closed position, should have the capability to hold fluid for at least five seconds there should be no branches in that portion of the vein wall which will ultimately be located in the stent. The sinus area is generally between boundaries 31.

Vein segment 20 may be obtained from a variety of suitable tissue sources such as mammalian or marsupial sources, including human or other primate, bovine, equine, porcine, canine, feline, kangaroo, and the like. Currently, a bovine jugular vein segment 20, including a venous valve, is preferred for percutaneous heart valve applications. Such bovine tissue is easily available in a variety of sizes, e.g., from 8 mm to 22 mm; is relatively biocompatible with human patients; has excellent intrinsic properties; has a low profile; is readily sutured to an expandable stent; retains its properties after crimping and re-expansion; and the leaflets are highly mobile, thin, and redundant. It is true that the venous wall of the bovine jugular vein tends to be too thick to be used without modification. However, in accordance with principles of the present invention, the wall thickness can be reduced with improved yields to a desired profile using laser ablation techniques without undue interference of the valve function.

For instance, the unmodified wall thickness between inner surface 30 and outer surface 32 may be on the order of about 1 to 3 mm. It is desired in many percutaneous heart valve applications to reduce this wall thickness, for instance, to about 0.5 mm or less. Dotted surface 34 shown in FIG. 1a generally shows the boundary between the wanted and unwanted tissue. Specifically, inner portion 36 corresponds to the modified vein segment 20 after laser machining so as to have the desired reduced wall thickness and/or reduced overall diameter, while outer wall portion 38 corresponds to the unwanted portion of vein segment 20 to be removed using laser ablation.

FIG. 1d shows the composite, percutaneous heart valve 1 that incorporates modified vein segment 20 after laser ablation techniques have been used to reduce its wall thickness to a desired profile. The modified vein segment 20 is now properly sized for insertion into a corresponding stent 10. A wide variety of stent structures may be used. One example of a suitable stent structure is a platinum-iridium stent that is currently used in similar, but conventionally made (i.e., made using manual techniques to reduce the profile of the venous wall), percutaneous heart valves available from NuMed Inc. by humanitarian device exemption. The associated, highly malleable stents have crimping and expansion properties currently labeled for one time use. These stent structures as used in the similar NuMed Inc. percutaneous heart valves also are illustrated in photographs in Boudjemline et al., "Future Trends: Percutaneous Valve Implantation: Past, Present and Future", Volume 3 No. 2 June-August 2002, the entirety of which is incorporated herein by reference for all purposes. See also Boudjemline et al., "Percutaneous Aortic Valve Replacement: Will We Get There?" Heart 2001; 86:705-706 (December), the entirety of which is incorporated herein by reference for all purposes.

The stent 10 as illustrated corresponds generally to that described in the above-cited Tower, et al., and Bonhoeffer et al. references. The stent 10 may be fabricated of platinum, iridium, stainless steel, other biocompatible metal, a metal alloy, an intermetallic composition, combinations of these, or the like. While stent 10 may be fabricated using wire stock as described in the above-cited Tower, et al. applications, an alternative approach machines the stent from a metal tube, as more commonly employed in the manufacture of stents. The stent 10 as illustrated, for use in conjunction with bovine jugular vein segments is typically 16-20 mm in diameter when expanded. The specifics of the stent 10 are not critical to the invention, and many other generally known cylindrical stent configurations may be used.

The stent 10, like most expandable cylindrical stents, generally takes the form of a series of zig-zag ring structures, e.g. 18, coupled longitudinally to one another to form a cylindrical structure. Each ring structure takes the form of a series of adjacent generally straight sections, e.g. 12, 14, which meet one another at a curved or angled junction, e.g. 16, to form a "V" or "U" shaped structure. For purposes of the present application, this structure will be referred to as a "V", and the included junction, e.g. 16, is referred to as the base of the "V". The relatively straight portions, e.g. 12, 14 of the stent between the bases of the "V"s are referred to herein as the "arms" of the "V" or simply as "arms". While the angled junctions as illustrated take the form of relatively sharply angled junctions, the "V" terminology is also intended to include more gradually curved junctions as well.

It should also be understood that although in the illustrated embodiment, the ring structures are coupled to one another at the base of each "V", stents employed according to the present invention may employ ring structures coupled to one another at fewer bases of their "V"s or coupled to one another by additional structures, such as longitudinal members, as disclosed in U.S. Pat. No. 6,773,455, issued to Allen, et al., U.S. Pat. No. 6,641,609, issued to Globerman and in U.S. Pat. No. 6,136,023, issued to Boyle.

The invention is also believed workable in other stents, including those in which wires are formed into zig-zags and wound spirally to produce a cylindrical structure, as in U.S. Pat. No. 6,656,219, issued to Wictor or woven stents as disclosed in U.S. Pat. No. 4,655,771, issued to Wallsten. FIG. 1d shows vein segment 20 positioned inside stent 10 and secured by sutures 40 in accordance with the description of the Bonhoeffer and Taitague Application, cited above.

FIGS. 2 through 7 show an illustrative system 100 and methodology that may be used to accomplish the reduction in wall thickness of vein segment 20 using laser ablation techniques. System 100 generally includes a laser source 130 and a stage assembly 102. Stage assembly 102 includes base 104, mounts 106 and 110, and a mandrel rotatably supported upon mounts 106 and 110. Vein segment 20 is mounted onto mandrel 114. Mandrel 114 may be formed from any suitable material or combination of materials. Conveniently, mandrel 114 is a glass tube, e.g., a test tube. The glass surface of a test tube is smooth, nonabrasive, hard, and scratch-resistant. Test tube glass also is substantially inert to reagents used with respect to vein segment 20. The glass is also compatible with laser processing. In such embodiments, using a glass mandrel with a 17 mm diameter has been found to be suitable for supporting vein segment 20 with a fit that is snug yet allows vein segment 20 to be relatively easily positioned on and removed from mandrel 114.

Mount 106 includes bore 108 to receive and provide a full bearing surface for one end of mandrel 114. Bore 108 may extend fully through mount 106, but more preferably extends only partially through mount 106 to provide a positive stop when mandrel 114 is seated. The top of mount 110 includes an open notch 112 suitably dimensioned to provide a partial bearing surface to rotatably support the other end of mandrel 114.

Mandrel 114 is rotatably coupled in any suitable fashion to a motor (not shown) or the like so that mandrel 114 can be rotatably driven. In those embodiments in which mandrel 114 is a test tube, a motor shaft 118 is coupled to stopper 120 fit into the end of mandrel 114, while the other end of the shaft 118 is coupled to the motor.

One or more additional optional features may be incorporated into stage assembly 102. As one example, reference mark(s) optionally may be used so that various tissues are positioned similarly and consistently on mandrel 114 from sample to sample. Such reference mark(s) may be conveniently provided on mandrel 114 itself.

As another option, it is known that the wall thickness of a typical vein section may vary. It is common, for instance, for the wall thickness associated with the sinus region to be relatively thin. If one were to reduce the profile of this region to the same degree as other, thicker-walled regions, the resultant wall thickness might be too thin or perhaps breached. Accordingly, it is desirable to identify such thin-walled regions on samples being processed. To help identify the thinner walled region(s) of a tissue sample, the interior of the mandrel 114 may include a light source (not shown) that may be used to illuminate the overlying tissue. Thinner-walled regions are relatively easy to identify as being more brightly illuminated than thicker walled regions.

Additionally, the operator or the system could position optional markers that indicate the boundaries of a thin-walled region such as the sinus area. Then, lesser amounts of tissue would be removed from these areas during a laser ablation treatment. This might be accomplished using less intense laser energy and/or less exposure to the laser energy, for instance. The placement of markers and control over the degree of laser ablation also could be automated. By way of example, a camera or other suitable sensing device could be used to identify and help set boundaries associated with the thinner areas. System settings could then be adjusted accordingly when such areas are subjected to ablation.

Laser source 130 outputs laser beam 132 toward vein segment 20. One or both of laser source 130 and stage assembly 102 are moveable relative to each other so that location at which laser beam 132 strikes vein segment 20 can be controllably varied. Preferably, laser source 130 is fixed and stage assembly 102 can be indexed in the x, y, and/or z axes to accomplish this.

Laser source 130 may include, but is not limited to, an excimer laser such as one producing laser energy with a wavelength of about 248 nm or 193 nm. The excimer lasers that produce laser energy at a wavelength of 248 nm are more preferred as these tend to be more economical and reliable. Alternative laser systems may include solid state lasers, such as frequency multiplied solid state lasers, flashlamp and diode pumped solid state lasers, and the like. Exemplary solid state lasers include UV solid state lasers producing wavelengths of approximately 188-240 nm such as those disclosed in U.S. Pat. Nos. 5,144,630, and 5,742,626; and in Borsuztky et al., *Tunable UV Radiation at Short Wavelengths* (188-240 nm) *Generated by Frequency Mixing in Lithium Borate, Appl. Phys.* 61:529-532 (1995). A variety of alternative lasers might also be used. A specific example of a suitable excimer laser operating at 248 nm is commercially available from Photo-Machining, Inc. under the trade designation Lambda LPX.

To accomplish tissue ablation the laser source is operated so that the laser output is relatively lower energy than is used for other kinds of tissue modification, e.g., tissue cutting or the like. Operating a laser source to output laser energy in a manner suitable for tissue ablation has been practiced, for instance, in connection with eye surgery and particularly with respect to ablation of the cornea. Those principles of laser operation as applied to ablation of eye tissue may be applied to accomplish tissue ablation in the context of the present invention.

Figure 4:
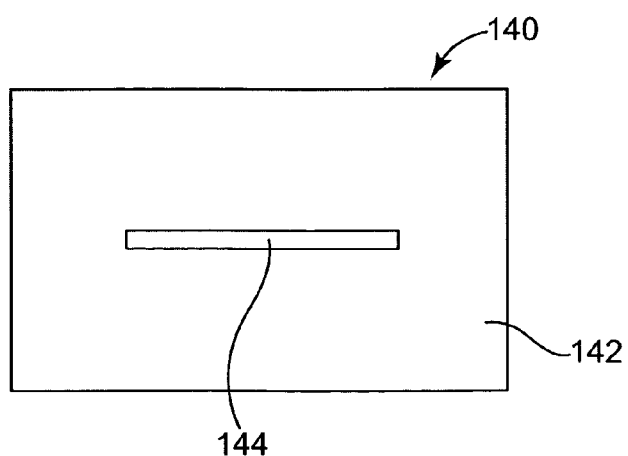
FIG. 4 schematically shows a mask used to control the size of the laser beam emitted from the laser source used in the system of FIG. 3.
Figure 3:
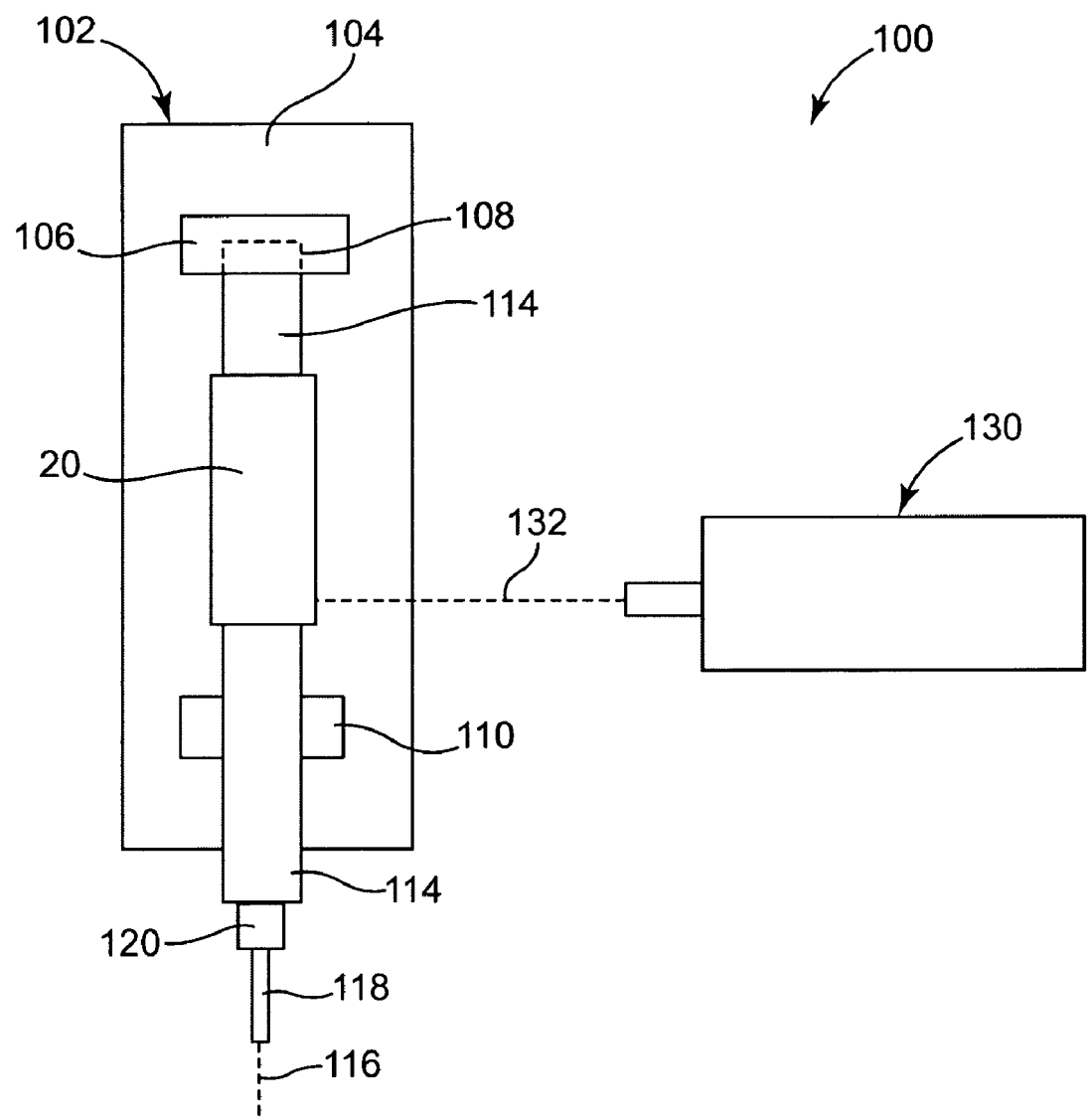
FIG. 3 shows a plan view of a laser machining system of the present invention incorporating the stage assembly of FIG. 2.

In those modes of practice in which the Model Lambda LPX excimer laser is used, one set of representative operational conditions to accomplish ablation of vein segment 20 are as follows:

Laser intensity: 0.38 J/cm2
Pulse energy: 367 mJ/pulse; homogenized
Frequency: 100 Hz
Rotational speed: 15°/sec
Masked beam This set of conditions uses a very low laser intensity setting under which the laser beam needs to make multiple sweeps of the target area to achieve the desired tissue reduction. Another representative set of very low laser intensity conditions that would be suitable is the following:

Laser intensity: 1.25 J/cm2
Pulse energy: 300 mJ/pulse
Frequency: 100 Hz
Rotational speed: 15°/sec corresponding to a tissue speed of about 2 mm/s
Masked beam On the other hand, the following set of laser intensity conditions was observed to cause undue tissue deformation using an excimer laser with a 248 nm output believed to be generally similar to the Model Lambda LPX excimer laser:

Laser intensity: 3.0 J/cm2
Pulse energy: 300 mJ/pulse
Frequency: 100 Hz
Rotational speed: 15°/sec corresponding to a tissue speed of about 2 mm/s
Masked beam At least one of two additional modifications of the laser output might also be desirable. Preferably, both modifications are used. Firstly, it is desirable to modify the laser energy with a homogenizer so that the energy density of the beam is more uniform. Additionally, as best shown in FIG. 4, it may be desirable to use a mask 140, which is not shown to scale, to control the footprint size of the beam. Mask 140 thus includes masked area 142 and window 144. The beam hitting masked area 142 is blocked, while the portion of the beam hitting window 144 is allowed to pass and then impact upon vein segment 20. The shape of window 144 is not critical, but its use allows better control over ablation as the footprint of the masked beam is more consistent. By way of example, one window 144 found to be suitable has a width of about 18.25 mm and a height of 0.625 mm. The resultant acicular window 144 having these dimensions is aligned with mandrel 114 so that the long dimension of the window 144 and the rotational axis 116 of the mandrel 114 are substantially parallel. This acicular shape has been found to be suitable for skivingly ablating tissue from vein segment 20.

Figure 5:
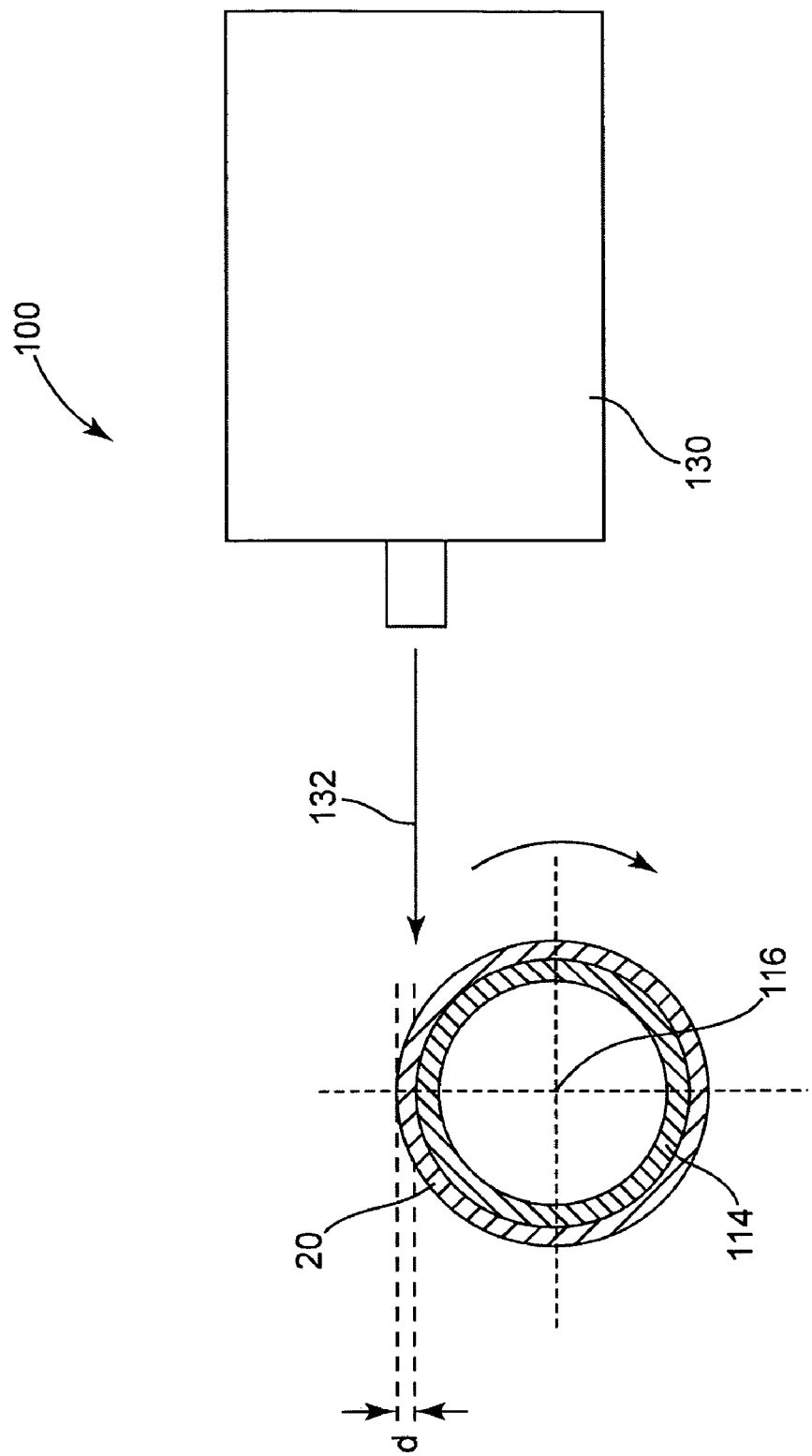
FIG. 5 schematically shows a side view of a portion of the system of FIG. 3 showing how the laser beam of the laser source obliquely strikes the tissue supported on the mandrel during one mode of practicing laser machining in the course of practicing the present invention.

The laser energy emitted by laser source 130 can be aimed at vein segment 20 in a variety of ways. According to a preferred approach as shown in FIG. 5, the beam is aimed obliquely at vein segment 20 in the sense that the beam is not aimed directly toward the center of rotation 116. According to one suitable oblique aiming technique, the laser beam is aimed generally tangentially toward the tissue. For reference, the distance d shown on FIG. 5 is generally equal to the thickness of tissue being processed. Alternately stated, the laser beam is aimed so that it is generally tangent to dotted surface 34 shown in FIGS. 1a and 1b when vein segment 20 is mounted on mandrel 114.

One illustrative method of using system 100 to reduce the profile of vein segment 20 using laser ablation will now be described. Stent 10 is also prepared for use. Laser ablation of vein segment 20 and preparation of stent 10 may be carried out sequentially or at least partially in parallel. With regard to stent 10, stent 10 is immersed in a suitable reagent to accomplish bioburden reduction (e.g., an aqueous solution containing 1% by weight gluteraldehyde and 20% by weight isopropyl alcohol) for at least three hours. After this period, the stent 10 is removed from the bioburden reagent, e.g., the reagent may be drained, and then the stent is stored in a suitable storage reagent (e.g., an aqueous solution containing 0.2% by weight gluteraldehyde) until subsequent use.

Next or in the meantime as the case may be, a vein segment 20 is provided and checked for suitability. Examples of tissue characteristics to evaluate include size, physical characteristics, no leakage or minimal leakage, no undue damage (holes, tears, etc.), no undue discoloration, gross hematoma, combinations of these, and the like. Additionally, the tissue should be free of branches for percutaneous heart valve applications, although branching may be acceptable for other applications. The vein segment 20 is trimmed, typically leaving a minimum of 15 mm of tissue from the tops of the commissures and bottom of the leaflets.

The vein segment 20 is also desirably subjected to suitable chemical fixation and/or bioburden reduction treatments. Chemical fixation helps to preserve the tissue, render it inanimate/inert, reduce the risk of rejection, and/or the like. Chemical fixation may occur by submerging the tissue in a suitable reagent for a period of about 3 hours under slight pressure and ambient temperature and then for 72 hours under ambient pressure and temperature. By way of example, a 0.2 weight percent gluteraldehyde solution at physiological pH and being phosphate buffered may be used for chemical fixation. This same solution also may be used to store the vein segment 20 up to sterilization, described below.

Bioburden reduction may be carried out by submerging the tissue in a suitable reagent for a period of 48 to 72 hours at ambient temperature. By way of example, an aqueous solution containing 1% by weight gluteraldehyde and 20% by weight isopropyl alcohol at physiological pH and being phosphate-buffered may be used for bioburden reduction. This solution also would be suitable for use as a packaging solution.

After these preparation steps, the vein segment 20 is slid onto position on mandrel 114. The leaflets 22 inside vein segment 20 help the vein segment 20 grip the mandrel 114 and help to prevent slipping during the ablation. Once mounted, the mandrel 114 bearing vein segment 20 is rotated at a suitable speed. Rotation is desirably slow, e.g., on the order of about 0.3 to 60 rpm, more preferably from about 0.5 to about 10 rpm, most preferably about 2.5 rpm (which corresponds to 15 degrees of rotation per second). The laser is aimed at vein segment 20 and the laser energy output is used to carry out the desired profile reduction via ablation. A typical vein segment 20 may have a starting wall thickness that is about 2 mm. Ablation may be carried out to reduce this to about 0.5 mm or less, typically about 0.4 mm.

Figure 6:
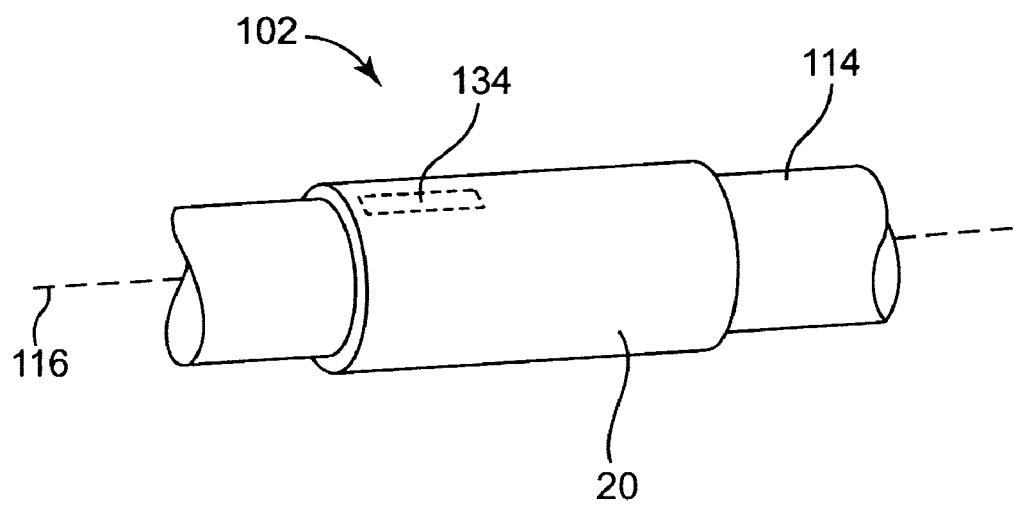
FIG. 6 is a schematic, close-up perspective view showing the vein of FIG. 1a supported on the mandrel of the system of FIG. 3, wherein the footprint of the laser beam obliquely striking the vein is shown.
Figure 7:
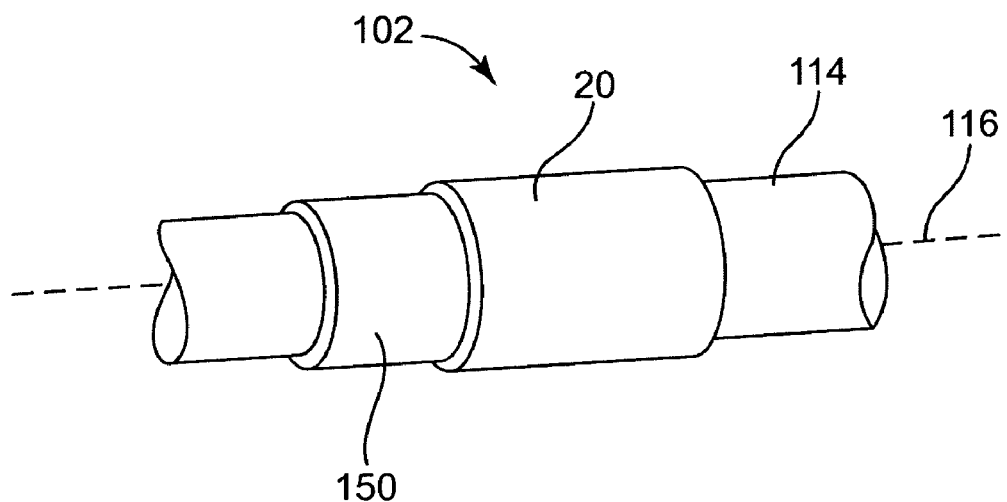
FIG. 7 schematically shows the vein and mandrel of FIG. 6 after a portion of the vein has been laser machined in accordance with the present invention.

FIGS. 6 and 7 illustrate one manner by which ablation occurs. FIG. 6 shows how the laser beam is initially aimed at one end of the rotating vein segment 20. Footprint 134 of laser beam upon the rotating vein segment 20 is shown as being proximal to one edge of segment 20. The laser beam energy is allowed to contact this portion of the vein segment 20 for a particular number of revolutions of the vein segment 20, as needed to accomplish the desired degree of ablation. As shown in FIG. 7, this treatment results in cleaned down region 150. The vein segment 20 is then indexed over so that the laser beam footprint 134 contacts the next portion of vein segment 20 to be ablated. This occurs for the appropriate time/turns to accomplish the desired profile reduction and then the vein segment 20 is indexed again. This is repeated until the desired tissue modification is accomplished.

Using the laser settings above, and aiming the laser generally tangentially toward the rotating tissue, using 30 rotations to ablate proximal to the tissue edges and 20 rotations with respect to the sinus area were suitable conditions. In another example, using 48 rotations proximal to the tissue edges and 20 rotations in the sinus area was suitable.

In contrast, when aiming the laser more directly toward the tissue generally at the axis of rotation, using 48 rotations proximal to the edges and 20 rotations with respect to the sinus area resulted in tissue tears. Using this direct ablation approach, using 53 rotations proximal to the edges and 30 rotations for the sinus resulted ablated through the tissue in some areas.

During the course of ablation, it is desirable to keep the vein segment 20 moist. To accomplish this, a suitable reagent can be sprayed, dripped or otherwise applied to vein segment 20. Yet, it is also desirable not to get vein segment 20 too wet, however, as this could increase processing time at a given energy level inasmuch as the reagent tends to absorb laser energy. Balancing such concerns, using approximately 5 mists/3 mins has been suitable. Examples of reagents that can be used for moistening include a conventional, aqueous saline solution as well as an aqueous gluteraldehyde solution containing, e.g., about 0.2% by weight of gluteraldehyde.

Optionally, ablation also may occur in a protected and/or controlled environment. This may or may not involve a protective enclosure (not shown) around system 100. In one embodiment, for example, ablation occurs within a clean room in the presence of a nitrogen assist. Nitrogen supplied at about room temperature at a pressure of about 10 psi represents one suitable nitrogen assist condition.

Some ablated tissues prepared in accordance with the present invention may have a slightly discolored surface. This was easily wiped off with a cloth, yielding a tissue surface having a color similar to that obtained from conventional, manual modification of a tissue. It is believed that the discoloration is a residue of ablated tissue.

After ablation is completed, the modified, ablated vein segment 20 is sutured to the stent 10. Preferred techniques for suturing are described in the Tower and Bonhoeffer documents cited herein as well as in Assignee's co-pending application cited herein. The resultant composite, percutaneous heart valve is inspected, sterilized, and packaged. Inspection generally involves size, physical characteristics, no leakage or minimal leakage, no undue damage (holes, tears, etc.), no undue discoloration, gross hematoma, proper stitching, no suture damage, proper placement of tissue in the stent, combinations of these, and the like. Sterilization may involve one or more techniques including a heat treatment and chemical sterilization. According to one sterilization methodology involving both a relatively low temperature heat treatment and a chemical treatment, the composite heart valve is immersed in the solution described above with respect to bioburden reduction and heated for 20 to 24 hours at 37° C. to 42° C. This may be done in a jar placed on its side. Details of stitching, inspecting, sterilizing, and packaging are further described in the Tower documents, Bonhoeffer documents, and Assignee's co-pending application cited herein, each of which is incorporated herein by reference in its respective entirety for all purposes. Representative delivery systems and methodologies for using the resultant heart valve 100 also are described in the Tower documents, Bonhoeffer documents, and Assignee's co-pending application cited herein While the discussion above describes a methodology by which tissue reduction is accomplished entirely using laser ablation, other embodiments of the invention may involve a combination of laser ablation with other techniques to modify the tissue. For example, manual techniques may be used to remove initial tissue layer(s), and then this could be followed up with tissue modification using laser ablation. This combination approach may be desired in some instances to reduce exposure of a tissue to the laser.

All patents, patent applications, patent publications, journal articles, and other publications mentioned herein are incorporated herein by reference in their entireties.

What is claimed is:

1. A method of making a composite medical device, comprising the steps of:
    a) providing a tissue comprising a leaflet-based valve;
    b) rotating the valved tissue;
    c) aiming a laser obliquely at the rotating tissue;
    d) using the obliquely aimed laser to ablate at least a portion of the tissue in a manner effective to reduce a wall thickness of the tissue along a length of the tissue; and
    e) integrating components comprising the ablated tissue and a nontissue component together to form the composite medical device.

2. The method of claim 1, wherein step (d) comprises using an excimer laser as a source of the laser energy.

3. The method of claim 1, wherein the laser has a laser energy output with a wavelength of about 248 nm.

4. The method of claim 1, wherein the tissue is a valved vein segment that is mounted on a rotating mandrel.

5. The method of claim 1, wherein the tissue is a bovine, valved vein segment.

6. The method of claim 1, wherein step (c) comprises aiming the laser tangentially at the rotating tissue.

7. The method of claim 6, wherein the nontissue component is a stent, the tissue is a valved vein segment, and step (e) comprises attaching the valved vein segment to the stent.

8. The method of claim 1, wherein step (b) comprises supporting the tissue on a rotatable support.

9. The method of claim 8, wherein the support comprises glass.

* * * * *